United States Patent [19]

Raulfs et al.

[11] Patent Number: 5,053,524
[45] Date of Patent: Oct. 1, 1991

[54] 3-AMINOPHENYLPENTANE-1,5-DIONES

[75] Inventors: Friedrich-Wilhelm Raulfs, Mannheim; Udo Mayer, Frankenthal; Andreas Oberlinner, Ludwigshafen, all of Fed. Rep. of Germany

[73] Assignee: BASF Aktiengesellschaft, Ludwigshafen, Fed. Rep. of Germany

[21] Appl. No.: 515,840

[22] Filed: Apr. 27, 1990

[30] Foreign Application Priority Data

Apr. 29, 1989 [DE] Fed. Rep. of Germany ....... 3914379

[51] Int. Cl.$^5$ .................. C07C 211/45; C07C 211/48; C07C 255/17; C07C 255/50
[52] U.S. Cl. .................................... 558/394; 558/415; 564/305; 564/428
[58] Field of Search ................ 564/305, 428; 558/415, 558/397

[56] References Cited

FOREIGN PATENT DOCUMENTS 0315491 5/1989 European Pat. Off. .

OTHER PUBLICATIONS

Chem. Ber., vol. 90, 1957, pp. 789-793, A. Treibs et al., "Uber Einen Chinopyrylium-Farbstoff".
Bull. Soc. Chim. France, (1970), No. 1, A. M. Baradel et al., "Configuratoin et Conformation des Produits d'Addition de la Benzylphenylcetone sur la Diphenyl-1,3 Propene-2, One-1 Trans", pp. 252-255.
Treibs et al., Ueber Einen Chinopyrilium Farbstoff, pp. 789-793, Verbindung II, Chemische Berichte, 90. Jahrgang, 1975.

Primary Examiner—Joseph Paul Brust
Attorney, Agent, or Firm—Oblon, Spivak, McClelland, Maier & Neustadt

[57] ABSTRACT

3-Aminophenylpentane-1,5-diones of the formula I

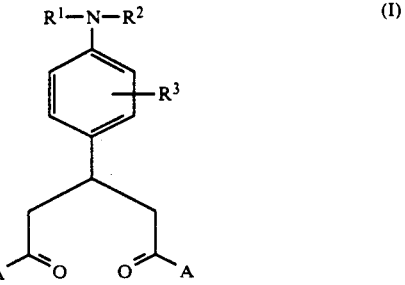

where
$R^1$ and $R^2$ are, independently of one another, hydrogen, $C_1$–$C_8$-alkyl, $C_4$–$C_8$-cycloalkyl, cyano-$C_2$–$C_4$-alkyl, hydroxy-$C_2$–$C_4$-alkyl, chloro-$C_2$–$C_4$-alkyl, phenyl-$C_1$–$C_2$-alkyl which can be substituted by chlorine, or phenyl which can be substituted by clorine or methyl, or $R^1$ and $R^2$ form, together with the nitrogen to which they are bonded, a heterocyclic radical which can contain further hetero atoms,
$R^3$ is hydrogen, fluorine, chlorine, $C_1$–$C_2$-alkyl or $C_2$–$C_5$-alkoxy or, if $R^3$ is ortho to —$NRR^2$, $R^3$ and $R^2$ together form $C_2$–$C_4$-alkylene, which can be substituted, or 1,2-phenylene and
A is naphthyl or a radical of the formula II

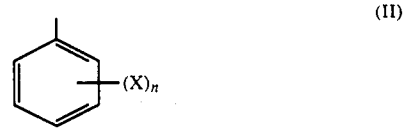

where
X is hydrogen, fluorine, chlorine, bromine, $C_1$–$C_5$-alkyl, hydroxyl, $C_1$–$C_5$-alkoxy, phenoxy, phenyl-$C_1$–$C_2$-alkoxy, cyano or phenyl and
n is 1 or 2,
with the proviso that $R^1$ and $R^2$ are not both methyl when A is phenyl, are described.

6 Claims, No Drawings

3-AMINOPHENYLPENTANE-1,5-DIONES

The present invention relates to novel 3-amino -phenylpentane-1,5-diones of the formula I

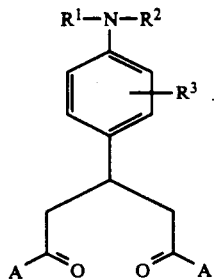

where
R$^1$ and R$^2$ are identical or different and, independently of one another, hydrogen, C$_1$–C$_8$-alkyl, C$_4$–C$_8$-cyclo alkyl, cyano-C$_2$–C$_4$-alkyl, hydroxy-C$_2$–C$_4$-alkyl, chloro- C$_2$–C$_4$-alkyl, phenyl-C$_1$–C$_2$-alkyl which can be substituted by chlorine, or phenyl which can be substituted by chlorine or methyl, or R$_1$ and R$_2$ form, together with the nitrogen to which they are bonded, a 5- or 6-membered saturated heterocyclic radical which can contain further hetero atoms,
R$^3$ is hydrogen, fluorine, chlorine, C$_1$–C$_2$-alkyl or C$_1$–C$_5$-alkoxy or, if R$^3$ is ortho to -NR$^1$R$^2$, R$^3$ and R$^2$ together form C$_2$–C$_4$-alkylene which can be substituted by 1 to 3 C$_1$–C$_4$-alkyls, or 1,2-phenylene and
A is naphthyl or a radical of the formula II

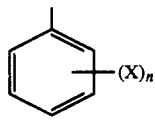

where
X is hydrogen, fluorine, chlorine, bromine, C$_1$–C$_5$-alkyl, hydroxyl, C$_1$–C$_5$-alkoxy, phenoxy, phenyl-C$_1$–C$_2$-alkoxy, cyano or phenyl and
n is 1 or 2,
with the proviso that R$^1$ and R$^2$ are not both methyl when
A is phenyl.

Chem Ber 90 (1957) 789–793 discloses the preparation of 3-(p-dimethylaminophenyl)-1,5-diphenylpentane -1,5-dione. This compound is used therein for the preparation of a pyridine.

The object of the present invention was to provide novel 3-aminophenylpentane-1,5-diones which are suitable for the preparation of triphenylcyclopentadienes or salts thereof.

We have found that this object is achieved by the 3-aminophenylpentane-1,5-diones of the formula I defined above.

All the alkyl and alkylene groups occurring in the abovementioned formula I can be either straight-chain or branched.

Examples of R$^1$, R$^2$ and X are methyl, ethyl, propyl, isopropyl, butyl, isobutyl, sec-butyl, tertbutyl, pentyl, isopentyl, neopentyl or tert-pentyl.

Further examples of R$^1$ and R$^2$ are hexyl, heptyl, octyl, 2-ethylhexyl, cyclobutyl, cyclopentyl, methylcyclopentyl, cyclohexyl, methylcyclohexyl, cycloheptyl, cyclooctyl, 2-cyanoethyl, 2- or 3-cyanopropyl, 2-hydroxyethyl, 2- or 3-hydroxypropyl, 2- or 4-hydroxybutyl, 2-chloroethyl, 2- or 3-chloropropyl, 2- or 4-chlorobutyl, benzyl, 1- or 2-phenylethyl or 4-chlorobenzyl.

R$^1$ and R$^2$ can also form, together with the nitrogen to which they are bonded, a 5- or 6-membered saturated heterocyclic radical which can contain further hetero atoms, eg. nitrogen, oxygen or sulfur. Examples are pyrrolidino, piperidino, morpholino, thiomorpholino, thiomorpholino, S, S-dioxide, piperazino or N-(C$_1$–C$_4$-alkyl)piperaxino such as N-methyl- or N-ethylpiperaxino.

Further examples of X, and of R$^3$, are methoxy, ethoxy, propoxy, isopropoxy, butoxy, isobutoxy, sec-butoxy, pentyloxy, isopentyloxy or neopentyloxy.

Further examples of R$^3$ are methyl or ethyl or, when R$^3$ is ortho to -NR$^1$R$^2$, R$^2$ and R$^3$ together are, for example, ethylene, 1,2- or 1,3-propylene, 1,2-, 1,3-, 2,3- or 1,4-butylene or 1,1,3-trimethyl-1,3-propylene.

Examples of A are phenyl, 4-chlorophenyl, 3,4-dichlorophenyl, 4-fluorophenyl, 3,4-difluorophenyl, 4-methylphenyl, 3-methylphenyl, 3,4-dimethylphenyl, 2,5-dimethylphenyl, 4-ethylphenyl, 4-propylphenyl, 4-isopropylphenyl, 4-butylphenyl, 4-tert-butylphenyl, 4-hydroxyphenyl, 4-methoxyphenyl, 3-methoxyphenyl, 2-methoxyphenyl, 2,4-dimethoxyphenyl, 2,5-dimethoxyphenyl, 3,4-dimethoxyphenyl, 3,5-dimethoxyphenyl, 4-ethoxyphenyl, 4-isopropoxyphenyl, 4-butoxyphenyl, 4-tert-butoxyphenyl, 4-phenoxyphenyl, 4-(2-phenylethoxy)phenyl, 4-cyanophenyl, 4-phenylphenyl, 1-naphthyl or 2-naphthyl.

When R$^1$ and R$^2$ in formula I are C$_1$–C$_8$-alkyl, preferred compounds are those in which R$^1$ is unbranched C$_1$–C$_8$-alkyl and R$^2$ is unbranched or branched C$_1$–C$_8$-alkyl.

Also preferred are 3-aminophenylpentane-1,5-diones of the formula I in which R$^3$ is hydrogen, methyl or methoxy.

Particularly preferred 3-aminophenylpentane-1,5-diones of the formula I are those in which R$^1$ and R$^2$ are, independently of one another, unbranched C$_1$–C$_4$-alkyl, cyanoethyl or benzyl, and R$^3$ is hydrogen.

Further particularly preferred 3-aminophenylpentane -1,5-diones of the formula I are those in which A is 1-naphthyl, 2-naphthyl or a radical of the formula II

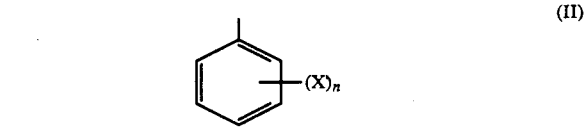

where
X is fluorine, chlorine, bromine, C$_1$–C$_5$-alkyl, hydroxyl, C$_1$–C$_5$-alkoxy, phenoxy, phenyl-C$_1$–C$_2$-alkoxy, cyano or phenyl and
n is 1 or 2.

Especially preferred are 3-aminophenylpentane 1,5-diones of the formula I in which A is 1-naphthyl, 2-naphthyl or a radical of the formula IIa

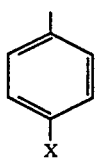

(IIa)

where
X is fluorine, chlorine, $C_1$–$C_5$-alkyl, $C_1$–$C_5$-alkoxy, cyano or phenyl.

Further especially preferred 3-aminophenylpentane-1,5-diones of the formula I are those in which $R^1$ and $R^2$ are, independently of one another, unbranched $C_1$–$C_4$-alkyl, cyanoethyl or benzyl and A is 4-chlorophenyl.

Further especially preferred 3-aminophenylpentane-1,5-diones of the formula I are those in which $R^1$ and $R^2$ are each methyl.

Also particularly important are the 3-aminophenylpentane-1,5-diones of the formula I in which A is phenyl, 4-chlorophenyl, 4-fluorophenyl, 4-methylphenyl, 4-methoxyphenyl, 1-naphthyl or 2-naphthyl.

The 3-aminophenylpentane-1,5-diones according to the invention can be obtained by conventional methods as described, for example, in Chem. Ber. 90 (1957) 789–793, by alkaline condensation of an aldehyde of the formula III with excess aryl ketone of the formula IV (in general 1.5 to 4 mol of IV per mol of III), where $R^1$, $R^2$, $R^3$ and A each have the abovementioned meaning, as shown in the diagram below

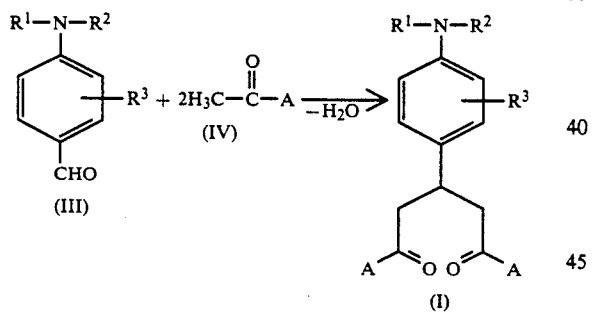

The reaction is advantageously carried out in the presence of a solvent, eg. an alcohol such as methanol, ethanol, propanol, isopropanol, butanol, isobutanol, methylglycol or 2-methoxypropanol, or mixtures thereof with water.

Alkali metal hydroxides such as sodium or potassium hydroxide, or alkali metal alcoholates such as sodium or potassium methanolate or ethanolate, which are preferably used in a 2-molar excess based on the aldehyde III, are particularly suitable agents for this condensation.

After an initial exothermic reaction, the suitable temperature range for the conversion is from 20° to 60° C. Further details of the preparation and isolation of the 1,5-diketones can be found in the examples.

The 3-aminophenylpentane-1,5-diones according to the invention are, as mentioned above, valuable intermediates for the synthesis of triphenylcyclopentadiene dyes or salts thereof.

Dyes of this type, which have the formula V or VI

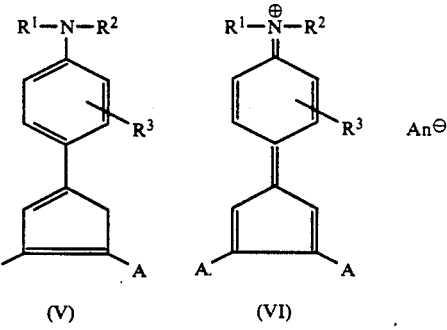

where $R^1$, $R^2$, $R^3$ and A each have the abovementioned meaning, and An$^\ominus$ is an anion, can be obtained from the 3-aminophenylpentane-1,5-diones I by, for example, treating the dione I with zinc in glacial acetic acid (see eg. Bull. Soc. Chim France (1970) 252–255), then converting the intermediate dihydroxycyclopentane derivative with acid (eg. hydrochloric or sulfuric acid) into the cyclopentadiene derivative V, which can then be converted by reaction with an oxidizing agent (eg. halogen such as chlorine, bromine or iodine, N-bromo- or. N-chlorosuccinimide, lead tetraacetate or iron(III) chloride) into the ionic dye VI.

The dyes of the formula V are suitable for dyeing polyester or polyamide fibers, and those of the formula VI are suitable for dyeing polyacrylonitrile fibers.

The examples which follow are intended to illustrate the invention in detail.

A) 3-Aminophenylpentane-1,5-dione

EXAMPLE 1

18 g of 50% by weight sodium hydroxide solution were added dropwise to 14.9 g of p-dimethylaminobenzaldehyde and 28.9 g of p-methylacetophenone in 250 ml of isopropanol while cooling. The reaction mixture was stirred at room temperature for 2 hours and then at 40° C. for 4.5 hours, and it was then cooled to 20° C. and filtered. The residue was washed first with isopropanol until the washings were pale yellow and then washed to neutrality with water. Isolated after drying were 27.3 g of 3-(p-dimethylaminophenyl)-1,5-bis(4-methylphenyl) pentane-1,5-dione. The colorless crystals melt at 125° to 126° C.

EXAMPLE 2

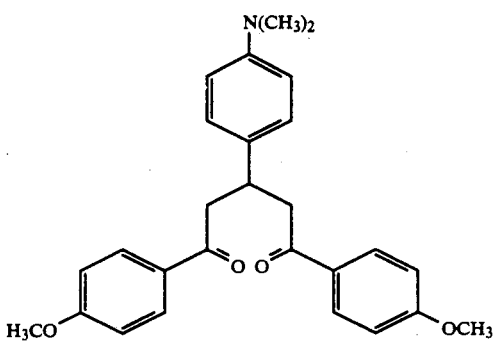

7.2 g of potassium hydroxide were dissolved in 150 ml of ethanol. 14.9 g of p-dimethylaminobenzaldehyde and 28.9 g of p-methoxyacetophenone were added and then the mixture was heated at 25° C. for 2 hours, 40°0 C. for 5 hours and under reflux for 7 hours The reaction mixture was worked up by pouring it into 1 l of water and 200 ml of ethyl acetate, and the pH was adjusted to 5 with glacial acetic acid. The organic phase was separated off and filtered to clarify. Ethyl acetate was distilled off at the water pump, and the residue was chromatographed on silica gel (eluent: 2:1 (v/v) toluene-/ethyl acetate). Isolated after recrystallization from cyclohexane were 2 g of colorless crystals of 3-(p-dimethylaminophenyl) -1,5-bis(p-methoxyphenyl)pentane-1,5-dione (melting point 70° to 72° C.).

EXAMPLE 3

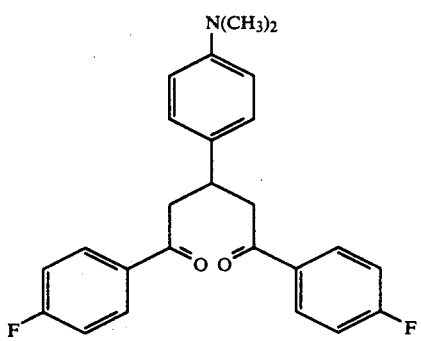

0 9 g of sodium hydroxide were dissolved in 150 ml of isopropanol. 14.9 g of p-dimethylaminobenzaldehyde and 29.7 g of p-fluoroacetophenone were added at 20° C. The mixture was stirred at 25° C. for 2 hours and then the precipitate was filtered off and the filtrate was slowly concentrated. 9.31 g of 3-(p-dimethylaminophenyl)-1,5-bis(p-fluorophenyl)pentane-1,5-dione precipitated out and melted at 92° C.

EXAMPLE 4

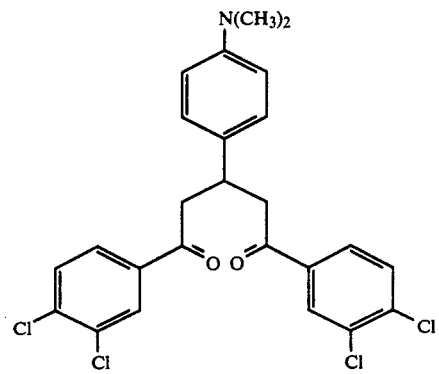

The method was that of Example 1 but 23.6 g of 3,4-dichloroacetophenone were used in place of p-methylacetophenone and reacted with 7.5 g of p-dimethylaminobenzaldehyde. 18 g of 3-(p-dimethylaminophenyl)-1,5-bis (3,4-dichlorophenyl)pentane-1,5-dione were obtained. The substance melts at 105° to 107° C.

Ketones of the formula A—CO—CH₃ were condensed with p-dimethylaminobenzaldehyde as in Example 1, resulting in the ketones of the formula

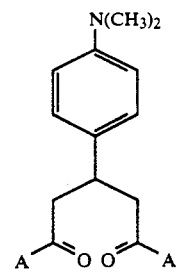

listed in Table 1 which follows.

TABLE 1

| Example No. | A | Amount of ketone (g) | Yield (g) | Melting range (°C.) |
|---|---|---|---|---|
| 5 | biphenyl | 49.0 | 45.2 | 194–200 |
| 6 | H₃C-phenyl (m-tolyl) | 16.8 | 12.1 | 85–87 |
| 7 | naphthyl | 21.3 | 15.9 | 129–130 |
| 8 | CH₃, O—CH₃, O—CH₃ substituted phenyl | 45.0 | 29.4 | 133–137 |
| 9 | CH₃, OCH₃ substituted phenyl | 18.8 | 9 | 109–111 |

TABLE 1-continued

| Example No. | A | Amount of ketone (g) | Yield (g) | Melting range (°C.) |
|---|---|---|---|---|
| 10 |  | 9.1 | 3.6 | 226–228 |

EXAMPLE 11

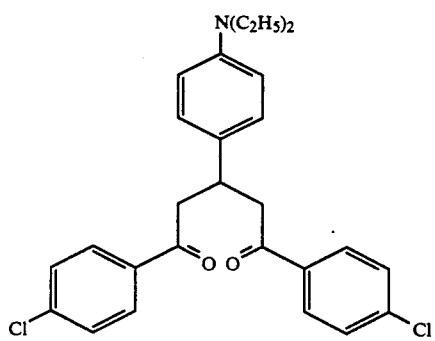

18 g of 50% by weight sodium hydroxide solution were added dropwise to 17.7 g of p-diethylaminobenzaldehyde and 33.3 g of p-chloroacetophenone in 150 ml of isopropanol at 20° C. The mixture was then sitrred at 20° C. for 2 hours and at 40° C. for 5 hours. The residue was filtered off and washed first with methanol until the washings were pale yellow and then with water until neutral. Drying resulted in 38.6 g of 3-(p-diethylamino phenyl)-1,5-bis(p-chlorophenyl)pentane-1,5-dione. The yellowish crystals melt at 140° C.

4-Chloroacetophenone was condensed with aldehydes of the formula B—CHO as in Example 2 to give the 1,5-diketones of the formula

listed in Table 2 which follows.

TABLE 2

| Example No. | B | Amount of aldehyde (g) | Yield (g) | Melting range (°C.) |
|---|---|---|---|---|
| 12 | (CH₃)₂N—⌬— | 14.9 | 38.3 | 103–104 |
| 13 | NCC₂H₄\N(CH₃)—⌬— | 18.8 | 13.4 | 89–96 |
| 14 | (NCC₂H₄)₂N—⌬— | 21.1 | 22.3 | 118–122 |
| 15 | [PhCH₂]₂N—⌬— | 15.1 | 17.2 | 93–100 |
| 16 | ClC₂H₄\N(C₂H₅)—⌬— | 10.6 | | |
| 17 | C₂H₅\N(CH₂Ph)—⌬— | 12.0 | 12.8 | 112–116 |
| 18 | C₄H₉\N(NCC₂H₄)—⌬— | 17 | 24.7 | 113 |

TABLE 2-continued

| Example No. | B | Amount of aldehyde (g) | Yield (g) | Melting range (°C.) |
|---|---|---|---|---|
| 19 | (N-ethyl carbazole with methyl substituent) | 11.2 | 22.2 | 103 |

EXAMPLE 20

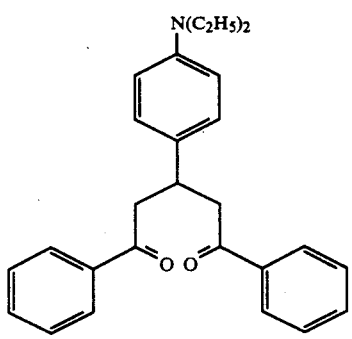

18 g of 50% by weight sodium hydroxide solution were added dropwise to 17.7 g of p-diethylaminobenzaldehyde and 26.4 g of acetophenone in 150 ml of ethanol at 20° C. The mixture was then stirred at 20° C. for 2 hours and at 50° C. for 5 hours. The precipitate was filtered off and washed with ethanol until the residue was only pale yellowish and then with water until neutral. 33.6 g of 3-(p-diethylaminophenyl)-1,5-diphenylpentane-1,5-dione were obtained. The almost colorless crystals melt at 110° C.

The compounds of the formula

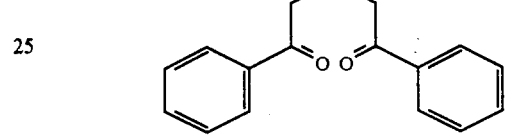

listed in Table 3 which follows were obtained as in Example 20.

TABLE 3

| Example No. | B | Amount of aldehyde (g) | Yield (g) | Melting range (°C.) |
|---|---|---|---|---|
| 21 | NCC$_2$H$_4$, H$_3$C–N–C$_6$H$_4$– | 9.4 | 8.0 | 110 |
| 22 | (NCC$_2$H$_4$)$_2$N–C$_6$H$_4$– | 11.4 | 16.3 | 115 |
| 23 | [C$_6$H$_5$–CH$_2$–]$_2$N–C$_6$H$_4$– | 15.1 | 14.6 | 139–141 |
| 24 | ClC$_2$H$_4$, C$_2$H$_5$–N–C$_6$H$_4$– | 10.6 | 11.4 | 94–95 |
| 25 | C$_2$H$_5$, C$_6$H$_5$–CH$_2$–N–C$_6$H$_4$– | 12.0 | 19.3 | 124 |
| 26 | C$_4$H$_9$, NCC$_2$H$_4$–N–C$_6$H$_4$– | 18.0 | 14.1 | 93–98 |

TABLE 3-continued

| Example No. | B | Amount of aldehyde (g) | Yield (g) | Melting range (°C.) |
|---|---|---|---|---|
| 27 | (N-ethylcarbazole structure) | 19.4 | 13.9 | 78–84 |

B) Preparation of the triphenylcyclopentadienes

EXAMPLE 28 a) 100 g of zinc powder were added a little at a time within 2 hours to 44 g of 1,5-bis(p-chlorophenyl)- 3-(p-dimethylaminophenyl)pentane-1,5-dione (Example 12) in 1,000 ml of glacial acetic acid at 80° to 87° C. The mixture was then stirred at 87° C. for a further 1.5 hours. The unreacted zinc was filtered off, and the reaction mixture was distilled under reduced pressure to remove glacial acetic acid. It was then diluted with 500 ml of water and adjusted to pH 4.2 with concentrated aqueous ammonia solution. The precipitate was filtered off with suction, dried under reduced pressure and recrystallized from xylene. Yield: 27.2 g of product of the formula

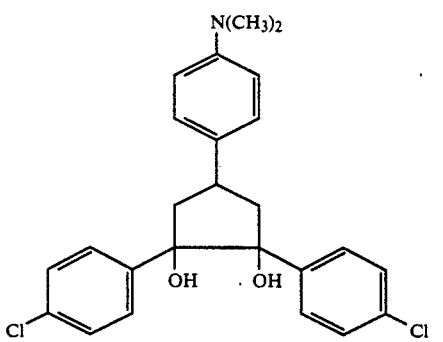

(Melting point: 114° to 118° C.)

b) The product from a) was introduced into 900 ml of 38% by weight hydrochloric acid and stirred at room temperature for 4 hours. The suspension was diluted with 1.8 l of water and filtered. The residue was taken up in 500 ml of methanol, and the pH was adjusted to 8 with concentrated aqueous ammonia solution. The resulting yellow crystals were recrystallized from ethanol. Yield: 16.2 g of product of the formula

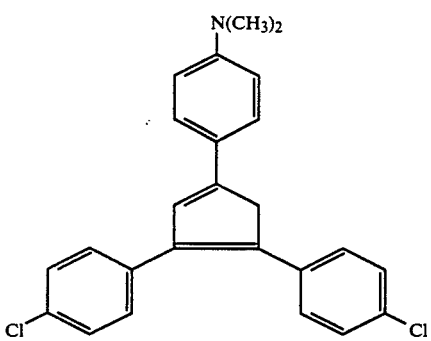

(Melting point: 138° to 139° C.) This product was used to dye polyester fabric (0.6% of dye on weight of fiber; dyebath at 130° C.; dyeing time: 60 minutes). The resulting dyeings were in shades of yellow.

c) 27 g of N-bromosuccinimide were added a little at a time in 5 minutes to a solution of the product from b) in 50 ml of ethyl formate at 50° C. The mixture was refluxed for 5 minutes with stirring and then the supernatant solution was decanted off and the residue was extracted by boiling with 50 ml of ethyl formate. The residue after decantation was stirred in ethyl acetate for 64 hours, filtered off and dried. 4.5 g of product of the formula

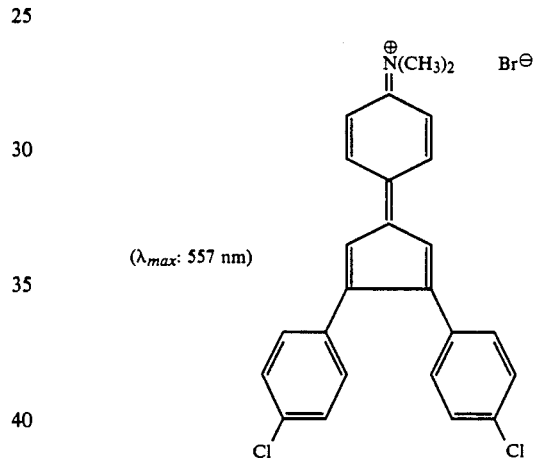

($\lambda_{max}$: 557 nm)

were obtained. This product was used to dye polyacrylonitrile fabric (0.6% of dye on weight of fiber; dyebath at 100° C.; dyeing time: 90 minutes). The resulting dyeings were in shades of violet.

We claim:

1. A 3-aminophenyl-pentane-1,5-dione of the formula I

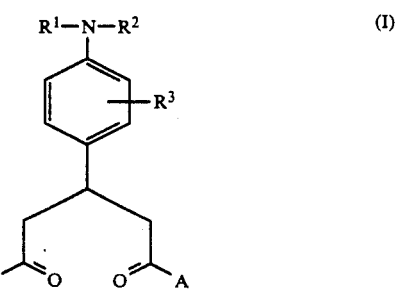

where $R^1$ and $R^2$ are indenpendently of one another hydrogen; $C_1-C_8$-alkyl; $C_4-C_8$-cycloalkyl; cyano-$C_2-C_4$-alkyl; hydroxy-$C_2-C_4$-alkyl; chloro-$C_2-C_4$-alkyl; phenyl -$C_1-C_2$-alkyl, which can be substituted by chlorine; or phenyl, which can substituted by chloirine or methyl;

$R^3$ is hydrogen, fluorine, chlorine, $C_1$–$C_2$-alkyl or $C_1$–$C_5$-alkoxy; and A is naphthyl or a radical of the formula II

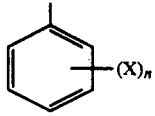

(II)

where

X is fluroine, chlorine, bromine, hydroxyl, $C_1$–$C_5$-alkoxy, pehnoxy, phenyl -$C_1$–$C_2$-alkoxy, cyano or phenyl and n is 1 or 2.

2. A 3-aminophenylpentane-1,5-dione as claimed in claim 1, wherein $R^1$ and $R^2$ are, independently of one another, unbranched $C_1$–$C_4$-alkyl, cyanoethyl or benzyl, and $R^3$ is hydrogen.

3. A 3-aminophenylpentane-1,5-dione as claimed in claim 1, wherein A is 1-naphthyl, 2-naphthyl or a radical of the formula IIa

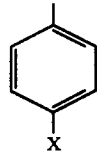

(IIa)

where is fluorine, chlorine, $C_1$–$C_5$-alkoxy, cyano or phenyl.

4. A 3-aminophenylpentane-1,5-dione as claimed in claim 1, wherein $R^1$ and $R^2$ are, independently of one another, unbranched $C_1$–$C_4$-alkyl, cyanoethyl or benzyl and A is 4-chlorophenyl.

5. A 3-aminophenylpentane-1,5-dione as claimed in claim 1, wherein $R^1$ and $R^2$ are each methyl.

6. A 3-aminophenylpentane-1,5-dione as claimed in claim 1, wherein said naphthyl is 1-naphthyl or 2-naphthyl.

* * * * *